(12) United States Patent
Choi et al.

(10) Patent No.: US 6,210,717 B1
(45) Date of Patent: Apr. 3, 2001

(54) BIODEGRADABLE MIXED POLYMERIC MICELLES FOR GENE DELIVERY

(75) Inventors: Young Kweon Choi, Taejeon; Jin Seok Kim, Seoul, both of (KR)

(73) Assignee: Samyang Corporation, Seoul (KR)

( * ) Notice: Subject to any disclaimer, the term of this patent is extended or adjusted under 35 U.S.C. 154(b) by 0 days.

(21) Appl. No.: 09/209,631

(22) Filed: Dec. 11, 1998

Related U.S. Application Data

(60) Provisional application No. 60/069,551, filed on Dec. 12, 1997.

(51) Int. Cl.[7] .................................................... A61K 9/50
(52) U.S. Cl. ............................................ 424/501; 424/502
(58) Field of Search ..................................... 424/501, 502

(56) References Cited

U.S. PATENT DOCUMENTS

| | | |
|---|---|---|
| 5,114,854 | 5/1992 | Bertholdt . |
| 5,273,525 | 12/1993 | Hofmann . |
| 5,501,662 | 3/1996 | Hofmann . |
| 5,744,153 * | 4/1998 | Yewey et al. .................. 424/426 |
| 5,752,974 * | 5/1998 | Rhee et al. .................... 606/214 |

OTHER PUBLICATIONS

Jean Haensler and Francis C. Szoka, Jr.; Polyamdoamine Cascade Polymers Mediate Efficient Transfection of Cells in Culture, pp. 372 to 379.

Jonathan L. Bramson, Frank L. Graham and Jack Gauldie; The use of adenoviral vectors for gene therapy and gene transfer in vivo, pp. 590 to 595.

Qin–Xin Zhou and Joschim Kohn; Preparation of Poly(L–serine ester): A structure Analogue of Conventional Poly(L–serine), pp. 3399 to 3406.

P.J. Southern and P. Berg; Transformation of Mammaliam Cells to Antibiotic Resistance with a Bacterial Gene Under Control of the SV 40 Early Region Promoter, pp. 327 to 341.

F.L. Graham and A. J. Van Der Eb; A New Technique for the Assay of Infectivity of Human Adenovirus 5 DNA, pp. 456 to 467.

Tim Mosmann; Rapid Colorimetric Assay for Cellular Growth and Surival; Application to Proliferation and Cytotoxicity Assays, pp. 55 to 63.

Alexander et al., "Infectivity of Ribonucleic Acid of Poliovirus on HeLa Cell monolayers", *Virology* 5 pp. 172–173 (1958).

Lee et al., "Detailed Analysis of Structures and Formulations of Cationic Lipids for Efficient Gene Transfer to the Lung", *Human Gene Therapy* 7 pp. 1701–1717 (1996).

Kabanov et al., "DNA Complexes With Polycations for the Delivery of Genetic Material Into Cells", *Bioconjugate Chem.* 6 pp. 7–20 (1995).

(List continued on next page.)

*Primary Examiner*—Carlos A. Azpuru
(74) *Attorney, Agent, or Firm*—Thorpe North & Western, LLP

(57) ABSTRACT

A biodegradable, mixed polymeric micelle used to deliver a selected nucleic acid into a targeted host cell contains an amphiphilic polyester-polycation copolymer and an amphiphilic polyester-sugar copolymer. The polyester-polycation copolymer forms an electrostatic interaction with polyanionic nucleic acids, and the polyester-sugar copolymer directs the micelle-nucleic acid complex to cells in vivo. Additional copolymers with similar properties may also be included. The composition improves delivery efficiency by providing a particulate gene carrier for which particle size and charge density are easily controlled by multivariate means. Various kinds of ligands and other functional compounds may be also be introduced using the composition. The composition may be used in a method for transforming a targeted host cell with a selected nucleic acid.

50 Claims, 1 Drawing Sheet

OTHER PUBLICATIONS

Wagner, "Transferrin–Polycation–DNA Complexes: The Effect of Polycations on the Structure of the Complex and DNA Delivery to Cells", *Proc. Natl. Acad. Sci. USA* 88 pp. 4255–4259 (1991).

Jobe et al., Surfactant Effects on Aerosolized and Instilled Adenoviral–Mediated Gene Transfer, *Human Gene Therapy* 7 pp. 697–704 (1996).

Wilson, "Gene Therapy for Cystic Fibrosis: Challenges and Future Directions", *J. Clin. Invest.* 96 pp. 2547–2554 (1995).

Ledley, "Nonviral Gene Therapy: The Promise of Genes as Pharmaceutical Products", *Hman Gene Therapy* 6 pp. 1129–1144 (1995).

Abdallah et al., "A Powerfull Nonviral Vector for In Vivo Gene Transfer Into the Adult Mammalian Brain: Polyethylenimine", *Human Gene Therapy* 7 pp. 1947–1954 (1996).

* cited by examiner

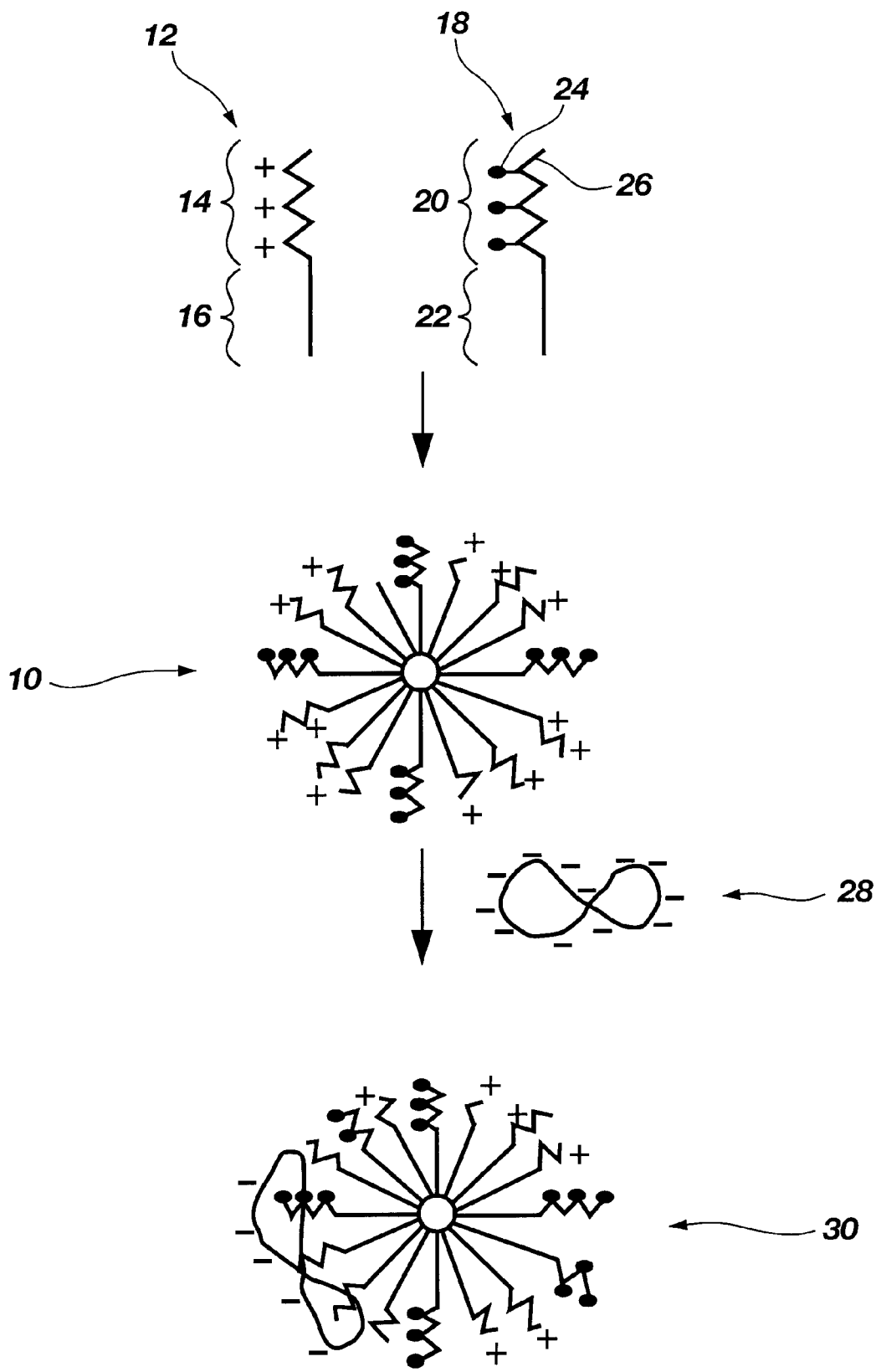

BIODEGRADABLE MIXED POLYMERIC MICELLES FOR GENE DELIVERY

CROSS-REFERENCE TO RELATED APPLICATIONS

This application claims the benefit of U.S. Provisional Application Ser. No. 60/069,551, filed Dec. 12, 1997.

BACKGROUND OF THE INVENTION

This invention relates to a system for transporting genes into eukaryotic cells. More particularly, the invention relates to a composition and a method for delivering a selected nucleic acid into a host cell using a biodegradable, mixed polymeric micelle comprising an amphiphilic polyester-polycation copolymer and an amphiphilic polyester-sugar copolymer.

Early efforts to identify methods of delivering nucleic acids into tissue culture cells began in the mid-1950's. H. E. Alexander et al., 5 Virology 172–173 (1958). Since then, steady progress has been made toward improving delivery of functional DNA, RNA, and antisense oligonucleotides (RNA function inhibitors) in vitro and in vivo. Substantial progress has been achieved during the last two decades due to the convergence of transfection technology and recombinant DNA technology in the late 1970's. This convergence began when calcium phosphate and diethylaminoethyldextran were applied for the expression of recombinant plasmids in cultured mammalian cells. P. J. Southern et al., 1 J. Mol. Appl. Gen. 327–341 (1982). Presently, delivery and expression of nucleic acids has become a topic that continues to capture scientific attention.

Some success has been achieved in delivering functional, non-replicating plasmids in vitro, however, the current methods for delivering functional, non-replicating plasmids in vivo are in their infancy. Transfection techniques include methods using insoluble inorganic salts, F. Graham, 52 Virology 456–462 (1973), cationic lipids, E. R. Lee et al., 7 Human Gene Therapy 1701–1717 (1996), cationic polymers, B. A. Demeneix et al., 7 Human Gene Therapy 1947–1954 (1996); A. V. Kabanov et al., 6 Bioconjugate Chem. 7–20 (1995); E. Wagner, 88 Proc. Natl. Acad. Sci. USA 4255–4259 (1991), viral vectors, A. H. Jobe, 7 Human Gene Therapy 697–704 (1996); J. Gauldie, 6 Current Opinion in Biotechnology 590–595 (1995), cell electroporation, U.S. Pat. No. 5,501,662 (1996); U.S. Pat. No. 5,273,525 (1993), and microinjection, U.S. Pat. No. 5,114,854 (1992). Each of the above-listed methods has specific disadvantages and limitations. The most widely studied gene transfer carriers are viral vectors, including retrovirus, adenovirus, adeno-associated virus, and herpes virus systems. Viral vectors have shown a high transfection efficiency compared to non-viral vectors, but their use in vivo is severely limited. Their drawbacks include targeting only dividing cells, random insertion into the host genome, risk of replication, and possible host immune reaction. J. M. Wilson, 96 J. Clin. Invest. 2547–2554 (1995).

Compared to viral vectors, nonviral vectors are easy to manufacture, less likely to produce immune reactions, and will not produce replication reactions. Dimethylaminoethyldextran-, calcium phosphate- and polycation-mediated transfection procedures have been used for tissue culture cells in the laboratory. Under some conditions, transfection efficiencies of close to 100% of the cells have been obtained in vitro. In general, however, nonviral vectors have been found to be ineffective for in vivo introduction of genetic material into cells and have resulted in relatively low gene expression. Various cationic amphiphiles have been extensively investigated and added to liposome formulations for the purpose of gene transfection. F. D. Ledley, 6 Human Gene Therapy 1 129–1144 (1995). To date, a cationic lipid system has been regarded as the most promising DNA transfection protocol, because it overcomes the problems with using viral vectors. However, transfection efficiency using cationic lipids is still not as high as with viral vectors, and complaints about cytotoxicity have been raised. Therefore, continuing investigation is required to find a new gene transfer protocol.

In view of the foregoing, it will be appreciated that development of a gene delivery system for in vivo use that is both safe and efficient would be a significant advancement in the art.

BREF SUMMARY OF THE INVENTION

It is an object of the present invention to provide a composition and method for delivering nucleic acids into cells.

It is also an object of the invention to improve delivery efficiency by providing a particulate gene carrier wherein particle size and charge density are easily controlled by multivariate means.

It is another object of the invention to provide a composition and a method for gene delivery wherein the gene carrier is biodegradable and biocompatible.

These and other objects are addressed by providing a carrier for delivery of a selected nucleic acid into a host cell, the carrier comprising a mixture of an amphiphilic polyester-polycation copolymer and an amphiphilic polyester-sugar copolymer. In a preferred embodiment of the invention, the polyester-polycation copolymer comprises about 5 to 95% by weight of the carrier. The polyester-sugar copolymer also preferably comprises about 5 to 95% by weight of the carrier. The polyester polycation copolymer can be either a diblock copolymer comprising a hydrophobic polyester block bonded to a hydrophilic polycation block by an amide linkage or a graft copolymer comprising a hydrophobic polyester portion and a hydrophilic cation portion. The polyester is preferably a member selected from the group consisting of poly(L-lactic acid), poly(D-lactic acid), poly(D-,L-lactic acid), poly(glycolic acid), poly(L-lactic-co-glycolic acid), poly(D-lactic-co-glycolic acid), poly($\epsilon$-caprolactone), polybutyrolactone, and polypropiolactone. More preferably, the polyester is poly(L-lactic acid). In a preferred embodiment of the invention the polyester has a molecular weight of about 500 to 10,000. The polycation is preferably a member selected from the group consisting of poly(L-serine ester), poly(D-serine ester), poly(L-lysine), poly(D-lysine), polyornithine, and polyarginine, and more preferably is poly(L-serine ester). In a preferred embodiment of the invention the polycation has a molecular weight of about 500 to 10,000.

The polyester-sugar copolymer comprises a hydrophobic polyester segment and a hydrophilic sugar segment. The polyester segment is preferably a member selected from the group consisting of poly(L-lactic acid), poly(D-lactic acid), poly(D-,L-lactic acid), poly(glycolic acid), poly(L-lactic-co-glycolic acid), poly(D-lactic-co-glycolic acid), poly($\epsilon$-caprolactone), polybutyrolactone, and polypropiolactone, and more preferably is poly(L-lactic acid). In a preferred embodiment of the invention the polyester segment has a molecular weight of about 500 to 10,000. The sugar segment can comprise either a polysaccharide or a glycosylated polymer. Such a glycosylated polymer preferably comprises at least one sugar moiety selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, and lactobionic acid, and more preferably is lactobionic acid. The polymer moiety of the glycosylated polymer is preferably selected from the group consisting of poly(L-serine ester), poly(D-serine ester), poly(L-lysine), poly(D-lysine), polyornithine, and polyarginine and more preferably is poly(L-serine ester), and more preferably is poly(L-lysine).

The carrier can optionally further comprise a copolymer comprising (a) a hydrophobic portion, (b) a hydrophilic portion bonded to the hydrophobic portion, and (c) a functional moiety coupled to the hydrophilic portion, wherein the functional moiety is a member selected from the group consisting of ligands, fusogenic agents, lysosomotrophic agents, nucleus localizing signals, and mixtures thereof. Such a ligand is preferably selected from the group consisting of transferrin, epidermal growth factor, insulin, asialoorosomucoid, inannose-6-phosphate, mannose, LewisX, sialyl LewisX, N-acetyllactosamine, galactose, glucose, and thrombomodulin; the fusogenic agent is preferably selected from the group consisting of polymixin B and hemaglutinin H2; and the nucleus localization signal is preferably T-antigen.

A composition for delivery of a selected nucleic acid into a host cell comprises a mixed-polymeric-micelle/nucleic-acid complex in an aqueous medium, wherein the mixed-polymeric-micelle/nucleic-acid complex comprises (a) a mixture of an amphiphilic polyester-polycation copolymer and an amphiphilic polyester-sugar copolymer, and (b) an effective amount of the selected nucleic acid.

A method for delivering a selected nucleic acid into a host cell comprises administering an effective amount of a mixed-polymeric-micelle/nucleic-acid complex in an aqueous medium, wherein the mixed-polymeric-micelle/nucleic-acid complex comprises (a) a mixture of an amphiphilic polyester-polycation copolymer and an amphiphilic polyester-sugar copolymer comprising a sugar moiety, and (b) an effective amount of said selected nucleic acid, such that the complex contacts the host cell and the sugar moiety triggers receptor mediated endocytosis of the mixed-polymeric-micelle/nucleic-acid complex, thus delivering the nucleic acid into the host cell.

BRIEF DESCRIPTION OF THE DRAWING

FIG. 1 is a schematic diagram of an electrostatic complex prepared from a self-assembled, mixed polymeric micelle and a nucleic acid.

DETAILED DESCRIPTION

Before the present composition and method for gene delivery are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a polyester-cationic copolymer" includes a mixture of two or more of such polyester-cationic copolymers, reference to "an oligonucleotide" includes reference to one or more of such oligonucleotides, and reference to "a sugar moiety" includes reference to two or more or such sugar moieties.

In describing and claiming the present invention, the following terminology will be used in accordance with the definitions set out below.

As used herein, "effective amount" means an amount of a micelle/nucleic-acid complex that is nontoxic but sufficient to provide the desired effect of delivering the nucleic acid into a selected cell at a reasonable benefit/risk ratio attending any medical treatment. An effective amount of a nucleic acid as used herein means an amount selected so as to provide the selected effect of the nucleic acid inside the cell, e.g. expressing mRNA, expressing a protein, inhibiting expression by antisense hybridization with mRNA, and the like. By effective amount of a carrier is meant an amount sufficient to form micelles in aqueous medium while forming a complex with the selected nucleic acid by electrostatic interaction.

The terms "polysaccharide" and "oligosaccharide" are used herein without any particular intended size limitation, unless a particular size is otherwise stated.

As used herein, "administering" and similar terms mean delivering the composition to the individual being treated such that the composition is capable of being circulated systemically to the parts of the body where the ligand or sugar portion of the composition can bind its cognate receptor or binding site. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable excipients include, for example, water, saline, dextrose, glycerol, ethanol, and the like; and if desired, minor amounts of auxiliary substances such as wetting or emulsifying agents, buffers, and the like can be added.

The present invention relates to a composition for forming self-assembled, mixed polymeric micelles for transporting gene constructs into specific eukaryotic cells. The polymeric micelle and nucleic acid form an electrostatic complex that is internalized in cells by receptor-mediated endocytosis. Suitable nucleic acids include DNA, RNA, and specific gene or RNA function inhibitors such as antisense oligonucleotides. The mixed polymeric micelle comprises two or more components, all of which are biodegradable, amphiphilic copolymers. The first component, a polyester-polycationic copolymer, forms an electrostatic interaction with polyanionic nucleic acids. The second component, a polyester-sugar copolymer, specifically directs the micelle-nucleic acid complex to selected cells in vivo. The invention optionally can further comprise one or more additional polyester-polycationic copolymers or polyester-sugar copolymers. The amphiphilic copolymers comprise block or graft copolymers having both hydrophilic and hydrophobic segments in the polymer chain. In the polyester-polycationic copolymer, the hydrophilic segment comprises a biodegradable, cationic polymer such as poly(serine ester). In the polyester-sugar copolymer, the hydrophilic segment comprises a polysaccharide or a monosaccharide- or oligosaccharide-bearing polymer. Biodegradable polyesters, such as poly(lactic acid), are used as the hydrophobic segment in both components.

In water, when a sufficient concentration of the two or more components is present, the components spontaneously aggregate into thermodynamically stable polymeric micelles. The micelle particles assume a spheroidal shape and possess, in essence, a double layer. The core "layer" forms by virtue of the hydrophobic interactions between the hydrophobic polyesters. Similarly, the surface "layer" forms by virtue of the corresponding hydrophilic interactions of the hydrophilic polycation and sugar with water. A net positive charge will exist around the surface of the micelle, since the hydrophilic segment of the first component is a polycation. The positive charge allows for an electrostatic interaction with a nucleic acid (i.e. a polyanion), which is essential for compacting and protecting the nucleic acid. The surface sugar groups may include ligands for directing the micelle-nucleic acid complex to the cells of a specific organ or tissue in vivo. Also, the sugar groups trigger receptor-mediated endocytosis resulting in the internalization and expression of the gene.

The particle size is crucial for the optimization of a gene delivery system, because the particle size often governs the transfection efficiency, cytotoxicity, and tissue targeting in vivo. F. C. Szoka, 4 Bioconjugate Chem. 372–379 (1993). Generally, the recommended size of a gene delivery particle should not exceed the size of viruses, thus enabling effective penetration of the gene delivery particle in tissue. In the present invention, the particle size can be easily varied by using different combinations of copolymers. The size and structure of individual copolymers determine the aggregation number, meaning the number of individual copolymers that will aggregate to form a micelle. Thus, size and structure partially control the particle size of a polymeric micelle. The particle size can be further controlled by conditions and methods of preparation of the particles. Charge density can also be easily controlled by varying the chemical composition of the polycationic copolymers, molecular weight and charge density of the polycationic segments, and mole ratio of the polycationic copolymer to the sugar-bearing copolymer. In addition, additional ionic and/or nonionic components can be incorporated to control the initial and residual charge densities.

Ligands that target specific cells and can be incorporated into a micelle include inter alia transferrin, epidermal growth factor (EGF), insulin, asialoorosomucoid, mannose 6-phosphate (targets monocytes), mannose (targets macrophages and some B-cells), Lewis$^x$ and sialyl Lewis$^x$ (targets endothelial cells), N-acetyllactosamine (targets T-cells), galactose (targets melanoma cells), glucose (targets colon carcinoma cells), and thrombomodulin (targets mouse lung endothelial cells). Other functional compounds that can be incorporated into a micelle include inter alia fusogenic agents such as polymixin B and hemaglutinin HA2, lysosomotrophic agents and nucleus localization signal (NLS) such as T-antigen. Functional compounds render the delivery and expression of exogenous nucleic acids more efficient, making the functional compounds important for successful gene delivery and expression. The functional compounds can be easily introduced with the micelle by: (1) creating a third copolymer component that bears the compound in a functional group and (2) coupling the copolymer to the surface of a pre-assembled polymeric micelle. Alternatively, a functional compound-bearing third component can be incorporated into a micelle along with the first and second component at the time the micelle originally forms. If so, then it may be preferable to use a copolymer wherein the functional group resides in the hydrophilic segment so that it is exposed in the micelle surface layer. Thus, various combinations of sugars, ligands and other functional compounds can reside in the second and subsequent components to maximize transfection efficiency of a micelle-nucleic acid complex. It is an advantage of the present invention that the kind and content of the functional group can be easily changed without limitation.

Micelles according to the present invention comprise biodegradable, biocompatible copolymers, resulting in non-immunogenicity and non-toxicity. The preferred copolymers disclosed herein degrade into non-toxic, small molecules subject to renal excretion and are inert during the required period of gene expression. Degradation occurs via simple hydrolytic and/or enzymatic reaction. Degradation through simple hydrolysis may be predominant when the backbone of a copolymer comprises ester bonds. Enzymatic degradation can become significant in the presence of certain organelles such as lysosomes. The degradation period can be varied from days to months by using polymers of different kinds and molecular weights. Thus, it can be seen how the use of biodegradable polymers for gene delivery can solve the problems of toxicity associated with polycationic gene carriers. Most polycationic gene carriers are known to be significantly cytotoxic, a serious effect in the case of long-term existence in the body. Therefore, it is preferable for the gene carrier to degrade into nontoxic products after fulfilling its role. The present invention uses biodegradable polyesters or polypeptides possessing safe and biocompatible degradation pathways. In addition, the highly-branched micellar structure of the present invention can further reduce cytotoxicity since branched polycations such as dendritic polyamidoamines are less cytotoxic than linear polycations. F. C. Szoka, 4 Bioconjugate Chem. 372–379 (1993). Accordingly, the advantageous components and structure of polymeric micelles according to the present invention can be appreciated regarding reduced cytotoxicity.

As shown in FIG. 1, a mixed, polymeric micelle 10 according to the present invention comprises two or more biodegradable, amphiphilic copolymers. The first copolymer 12 is a polyester-polycation block or graft copolymer comprising a hydrophilic polycation segment 14 and a hydrophobic polyester segment 16. The hydrophilic polycation segment 14 should be large enough to endow water solubility to the copolymer. The first copolymer can be prepared as a di-, tri- or multi-block or graft copolymer, but preferably as di-block or graft copolymer. The polyester segment 16 is preferably poly(L-lactic acid), poly(D-lactic acid), poly(D-, L-lactic acid), poly(glycolic acid), poly(L-lactic-co-glycolic acid), poly(D-lactic-co-glycolic acid), poly(ε-caprolactone), polybutyrolactone, or polypropiolactone, but more preferably poly(L-lactic acid). The polycation segment 14 is preferably a polycation wherein the monomer units are connected by an ester or amide linkage such as poly(L-serine ester), poly(D-serine ester), poly(L-lysine), poly(D-lysine), polyornithine, or polyarginine, but more preferably poly(L-serine ester) due to its greater biodegradability.

The second copolymer 18 is a polyester-sugar block or graft copolymer, where the sugar segment 20 is large enough to solubilize the copolymer in water. The polyester segment 22 can be the same as in the first copolymer 12 or it may be different, and is preferably selected from the same group indicated above for the polyester segment 16 of the first copolymer 12. The sugar segment 20 is preferably a polysaccharide or a glycosylated polymer, but more preferably is a glycosylated polymer. As illustratively shown in FIG. 1, a glycosylated polymer is prepared by coupling one or more monosaccharides or oligosaccharides or derivatives thereof 24 to a polymer 26 bearing one or more functional pendent groups such as hydroxyl, carboxyl, or amino groups. The monosaccharides or oligosaccharides or derivatives thereof are preferably galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, and lactobionic acid. The conjugation of an acid form of the sugar to a polycationic polymer is most preferable. Thus, the most preferred embodiment of the present invention constitutes lactobionic acid (4-O-β-D-galactopyranosyl-D-gluconic acid) coupled to poly(L-serine ester) or poly(L-lysine). The galactosyl unit of lactose conveniently targets hepatocyte cells because of the high affinity and avidity of the galactose receptor on the cells.

As further shown in FIG. 1, mixing of the mixed polymeric micelle 10 with a selected nucleic acid 28 results in electrostatic bonding of the negative charges on the nucleic acid to the positive charges on the micelle to result in a micelle-nucleic acid complex 30.

A mixed polymeric micelle is formed from the two or more copolymers mixed in a properly designed weight ratio. In other words, the particle size should range from approximately 10 to 100 nm and will depend on the polymer composition and the mixing ratio of the two or more copolymers. The most preferred embodiment of the present invention effectively delivers a selected nucleic acid into hepatocytes by endocytosis mediated by a galactosyl receptor on the surface of the cells. Nucleic acid transfer to other cells can be carried out by matching a cell having a selected receptor with a selected sugar. For example, the mixed micelle can be prepared from a mannose-pendent copolymer for transfecting macrophage, N-acetyllactosamine for transfecting T-cells, and glucose for transfecting colon carcinoma cells.

Thus, the present invention provides a biodegradable, non-toxic and non-viral vector for transferring a selected nucleic acid into hepatocyte cells, specifically, and other cells, generally. In addition, the present invention provides an easy and efficient way to construct a diverse and well-defined micelle structure and to functionalize the surface with diverse sugar ligands and fusogenic agents, such as endosomal disrupting peptides (EDP).

EXAMPLE 1

In this example, preparation of a mixed polymeric micelle from poly(L-lactic acid)-poly(L-serine ester) diblock copolymer and poly(L-lactic acid)-poly(N-lactosyl-L-serine ester) diblock copolymer is described.

Poly(N-benzyloxycarbonyl-L-serine ester).

First, 4-(dimethylamino)pyridium 4-toluenesulfonate was prepared by reacting equimolar amounts of 4-(dimethylamino)pyridine and p-toluene sulfonic acid in anhydrous benzene according to the procedure described in 23 Macromolecules 65–70 (1990) (hereby incorporated by reference). N-benzyloxycarbonyl (N-CBZ) serine (2.392 g) was placed in a two-neck round bottom flask containing a stirring bar and fitted with a nitrogen manifold and a rubber septum and dissolved by adding tetrahydrofuran (30 ml) via a syringe in a nitrogen atmosphere. A methylene chloride solution (80 ml) of the 4-(dimethylamino)pyridium 4-toluenesulfonate (2.94 g) and diisopropyl carbodiimide was successively added via syringe, and the reaction mixture was stirred for 1 to 5 days at room temperature. Upon completion of the reaction, the reaction mixture was filtered to remove the diisopropyl urea and then dried to completion using a rotary evaporator. The reaction product was obtained by recrystallization in methanol and characterized by gel permeation chromatography (GPC) using polystyrene standards.

Poly(L-lactic acid).

Three g of L-lactic acid was placed in a single-neck round bottom flask containing a stirring bar and equipped with a vacuum distillation apparatus. The reaction flask was flushed thoroughly with nitrogen, and then the mixture was heated at 160° C. under vacuum (5 mmHg). The reaction time was varied from 1 hour to 10 hours to obtain diverse molecular weights of poly(L-lactic acid). The product was obtained by precipitation in chloroform solution with a large excess amount of methanol and characterized by GPC using polystyrene standards.

Poly(L-lactic acid)-poly(L-serine ester) diblock copolymer.

One g of poly(L-lactic acid) (MW 1200) was dissolved in tetrahydrofuran, and a twice molar amount of diaminoethane was added in the presence of dicyclohexylcarbodiimide to yield amine-terminated poly(L-lactic acid). After 2 hours of stirring at room temperature, the reaction product was obtained by precipitation in methanol. The amine-terminated poly(L-lactic acid) was then reacted with an equimolar amount of poly(N-benzyloxycarbonyl-L-serine ester) (MW 2900) in dimethylformamide at room temperature using dicyclohexylcarbodiimide, followed by the removal of the benzyloxycarbonyl group using catalytic hydrogenation. 23 Macromolecules 3399–3406 (1990).

Poly(L-lactic acid)-poly(N-lactosyl-L-serine ester) diblock copolymer.

A solution of lactobionic acid (1.33 g) in dry tetrahydrofuran (50 ml) was neutralized with an equimolar amount of triethylamine (500 ml) followed by addition of isobutyl chlorocarbonate (500 ml) at room temperature. After 10 minutes of stirring, the reaction mixture was added into a dimethylsulfoxide solution (50 ml) of poly(L-lactic acid)-poly(L-serine ester) (0.67 g) and allowed to stir for 20 minutes at room temperature. The reaction product was obtained by filtration and precipitation in diethyl ether and was purified by dialysis against water using SPECTRAPOR membrane tubing (MW cutoff 1,000).

Mixed polymeric micelle.

A mixture of poly(L-lactic acid)-poly(L-serine ester) and poly(L-lactic acid)-poly(N-lactosyl-L-serine ester) was made in phosphate buffer (pH 7.4) and subjected to the transfection procedure of Example 4 using a β-galactosidase gene and HepG2 cells.

EXAMPLE 2

In this example the preparation of a mixed polymeric micelle from poly(L-lactic acid)-poly(L-serine ester) diblock copolymer and poly(L-lactic acid)-poly(N-lactosyl-L-serine ester) diblock copolymer is described.

The procedure was carried out as in Example 1, except that amine-terminated poly(L-lactic acid) was synthesized by ring-opening polymerization of L-lactide initiated with N-trityl ethanolamine. N-trityl ethanolamine was prepared by stirring trityl chloride (3 g) in ethanolamine (20 ml) at room temperature. The precipitated product was obtained by filtration and purified by recrystallization in methanol-water (9:1). L-lactide polymerization was initiated with N-trityl ethanolamine in refluxed toluene in the presence of a catalytic amount of stannous octoate. Poly(L-lactic acid) was obtained by precipitation in a large excess amount of diethyl ether. The trityl group was removed using 0.1 M trifluoroacetic acid in dioxane.

EXAMPLE 3

In this example the preparation of a mixed polymeric micelle from poly(L-lactic acid)-poly(L-lysine) graft copolymer and poly(L-lactic acid)-poly(N-lactosyl-L-lysine) graft copolymer is described.

The mixed polymeric micelle was prepared from poly(L-lactic acid)-poly(L-lysine) and poly(L-lactic acid)-poly(N-lactosyl-L-lysine) copolymers. Poly(L-lysine) (MW 2700) was obtained from Sigma Chemical Co.(St. Louis, Mo.), and poly(L-lactic acid) (MW 1200) was prepared by polycondensation in accordance with the procedure of Example 1. The carboxyl end group of poly(L-lactic acid) was activated with an equimolar amount of isobutychloroformate and then reacted with an equimolar amount of poly(L-lysine) to yield poly(L-lactic acid)-poly(L-lysine) copolymer. The poly(L-lactic acid)-poly(N-lactosyl-L-lysine) was prepared by reacting lactobionic acid with poly(L-lactic acid)-poly(L-lysine) according to the procedure of Example 1. Various combinations of poly(L-lactic acid)-poly(L-lysine) and poly(L-lactic acid)-poly(N-lactosyl-L-lysine) were prepared in a phosphate buffer (pH 7.4) and subjected to the transfection procedure of Example 4 using a β-galactosidase-encoding gene for human liver carcinoma HepG2 cells.

EXAMPLE 4

In this example a transfection and cytotoxicity test of mixed polymeric micelles using HepG2 cells is described.

In vitro transfection efficiency of mixed polymeric micelles was tested on human liver carcinoma cells (HepG2) grown in MEM medium with 10% fetal bovine serum. Cells were harvested and counted using a hemacytometer and plated in 96-well plates at a density of $2 \times 10^5$ cells/ml. One day later, various formulations of micelle-gene complexes comprising poly(L-lactic acid)-poly(L-lysine) and/or poly(L-lactic acid)-poly(N-lactosyl-L-lysine) copolymers and pSV-β-gal plasmid DNA (Promega Corp., Madison, Wis.; EMBL accession No. X65335) were freshly prepared 30 minutes before transfection. The growth medium in each well of the 96-well plates was replaced by fresh growth medium without serum and the micelle-gene complexes were added to a final volume of 10 μl. After a 4 hour-incubation, the growth medium was replaced with a serum-containing medium and cells were further incubated for an additional 44 hours at 37° C. in a 5% $CO_2$ incubator. Cells were then harvested using 0.25% trypsin-EDTA treatment and cell lysates were obtained by adding 100 μl of 1× lysis buffer (Promega, Madison, Wis.) to each well.

Plasmid pSV-β-gal is a positive control vector for monitoring transfection efficiencies of mammalian cells. The pSV-β-gal plasmid contains a SV40 early promoter and enhancer sequence, transcription start sites, *E. coli* lacZ coding region encoding β-galactosidase, and SV40 small T antigen polyadenylation signals. SV40 early promoter and enhancer drive the transcription of the lacZ gene.

Transfection efficiency was measured by determining the β-galactosidase enzyme activity in cell lysates. Mixtures of equal amounts of cell lysates and o-nitrophenyl-β-D-galactopyranoside (ONPG, 1.33 mg/ml) in a 2× assay buffer (Promega) were incubated at 37° C. for 4 hours. The reaction was terminated by adding 150 μl of 1 M sodium carbonate solution to each well, and the absorbance at 420 nm was read with a spectrophotometer for the β-galactosidase activity. LIPOFECTIN reagent (GIBCO/BRL, Gaithersburg, Md.) was used as a control to compare the transfection efficiency. LIPOFECTIN reagent is a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water.

Cytotoxicity of the mixed polymeric micelles to HepG2 cells was determined by the MTT colorimetric assay originally described by T. Mosmann, Rapid Colorimetric Assay for Cellular Growth and Survival: Application to Proliferation and Cytotoxicity Assays, 65 J. Immunol. Methods 55–63 (1983). Briefly, cells were harvested from exponentially growing culture and plated in 96-well plates at $2 \times 10^5$ cells/ml density. After a 24 hour-incubation period, cells were treated with varying amounts of poly(L-lactic acid)-poly(L-lysine) and/or poly(L-lactic acid)-poly(N-lactosyl-L-lysine) copolymer solution in the absence of serum. After a 4 hour-incubation, the growth medium was replaced with serum-containing growth medium and cells were further incubated for an additional 44 hours at 37° C. in a 5% $CO_2$ incubator. Then, 25 μl of 3-[4,5-dimethylthiozol-2-yl]-2,5-diphenyltetrazolium bromide (MTT) solution (final concentration, 0.5 mg/ml) was added to each well, followed by 4 hours of incubation at 37° C. Growth medium was carefully removed and 150 μl of DMSO was added to dissolve the formed formazan crystal. The optical density (OD) was measured at 570 nm using a Bio-Tek EL-33 11 microplate reader (Bio-Tek Instrument, Winooski, Vt.). Cell viability (%) was calculated according to the following equation: Viability (%)=[$OD_{570}$ (sample)/$OD_{570}$ (control)]× 100, where the $OD_{570}$ (control) represents the measurement from the wells treated with PBS buffer only and the $OD_{570}$ (sample) represents the measurement from the wells treated with varying amounts of polymer.

As shown in Table 1, transfection efficiency of mixed polymeric micelles according to the present invention was as good as LIPOFECTIN reagent in HepG2 cells in vitro in the absence of serum. Cytotoxicity of mixed polymeric micelles for HepG2 cells was much lower or vanishingly small as compared to LIPOFECTIN reagent, as shown in Table 2, suggesting that these micelles have broad applications to other tissues or organs, as well as to hepatocytes.

TABLE 1

Relative transfection efficiency (%) of mixed, polymeric micelles consisting of poly(L-lactic acid)-poly(L-lysine) (PLL) and poly(L-lactic acid)-poly(N-lactosyl-L-lysine) (PLGL) compared to LIPOFECTIN reagent using HepG2 cells.

| | Composition | Total weight of micelle used | | | |
|---|---|---|---|---|---|
| Code | (PLGL Wt %) | 5 μg | 10 μg | 20 μg | 30 μg |
| PLLGL 30 | 30 | 71 | 74 | 67 | 58 |
| PLLGL 50 | 50 | 64 | 62 | 63 | 71 |
| PLLGL 70 | 70 | 73 | 66 | 66 | 74 |

TABLE 2

Cytotoxicity (100-cell viability (%)) of mixed, polymeric micelles consisting of poly(L-lactic acid)-poly(L-lysine) (PLL) and poly(L-lactic acid)-poly(N-lactosyl-L-lysine) (PLGL) compared to LIPOFECTIN reagent using HepG2 cells.

| Code | Composition (PLGL Wt %) | Total weight of micelle used | | | |
|---|---|---|---|---|---|
| | | 5 μg | 10 μg | 20 μg | 30 μg |
| PLLGL 0 | 0 | 23 | 30 | 24 | 19 |
| PLLGL 30 | 30 | 7 | 0 | 0 | 17 |
| PLLGL 50 | 50 | 0 | 0 | 7 | 45 |
| PLLGL 70 | 70 | 0 | 0 | 5 | 61 |
| PLLGL 100 | 100 | 0 | 0 | 22 | 63 |
| LIPOFECTIN | — | — | — | 24 | 59 |

We claim:

1. A carrier for delivery of a nucleic acid into a host cell comprising a mixture of an amphiphilic polyester-polycation copolymer and an amphiphilic polyester-sugar copolymer.

2. The carrier of claim 1 wherein said polyester polycation copolymer is a diblock polymer comprising a hydrophobic polyester block bonded to a hydrophilic polycation block by amide linkage.

3. The carrier of claim 2 wherein said polyester block is a member selected from the group consisting of poly(L-lactic acid), poly(D-lactic acid), poly(D-,L-lactic acid), poly(glycolic acid), poly(L-lactic-co-glycolic acid), poly(D-lactic-co-glycolic acid), poly($\epsilon$-caprolactone), polybutyrolactone, and polypropiolactone.

4. The carrier of claim 3 wherein said polyester block is poly(L-lactic acid).

5. The carrier of claim 3 wherein said polyester block has a molecular weight of about 500 to 10,000.

6. The carrier of claim 2 wherein said polycation block is a member selected from the group consisting of poly(L-serine ester), poly(D-serine ester), poly(L-lysine), poly(D-lysine), polyornithine, and polyarginine.

7. The carrier of claim 6 wherein said polycation block is poly(L-serine ester).

8. The carrier of claim 6 where polycation block has a molecular weight of about 500 to 10,000.

9. The carrier of claim 1 wherein said polyester-sugar copolymer comprises a hydrophobic polyester segment and a hydrophilic sugar segment.

10. The carrier of claim 9 wherein said polyester segment is a member selected from the group consisting of poly(L-lactic acid), poly(D-lactic acid), poly(D-,L-lactic acid), poly(glycolic acid), poly(L-lactic-co-glycolic acid), poly(D-lactic-co-glycolic acid), poly(E-caprolactone), polybutyrolactone, and polypropiolactone.

11. The carrier of claim 10 wherein said polyester segment is poly(L-lactic acid).

12. The carrier of claim 10 wherein said polyester segment has a molecular weight of about 500 to 10,000.

13. The carrier of claim 9 wherein said sugar segment comprises a polysaccharide.

14. The carrier of claim 9 wherein said sugar segment comprises a glycosylated polymer.

15. The carrier of claim 14 wherein said glycosylated polymer comprises at least one sugar moiety selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, and lactobionic acid.

16. The carrier of claim 15 wherein said sugar moiety is lactobionic acid.

17. The carrier of claim 14 wherein said glycosylated polymer comprises a polymer moiety selected from the group consisting of poly(L-serine ester), poly(D-serine ester), poly(L-lysine), poly(D-lysine), polyornithine, and polyarginine.

18. The carrier of claim 17 wherein said polymer moiety is poly(L-serine ester).

19. The carrier of claim 17 wherein said polymer moiety is poly(L-lysine).

20. The carrier of claim 1 comprising about 5 to 95% by weight of said polyester-polycation copolymer.

21. The carrier of claim 1 further comprising a copolymer comprising (a) a hydrophobic portion, (b) a hydrophilic portion bonded to the hydrophobic portion, and (c) a functional moiety coupled to the hydrophilic portion, wherein said functional moiety is a member selected from the group consisting of ligands, fusogenic agents, lysosomotrophic agents, nucleus localizing signals, and mixtures thereof.

22. The carrier of claim 21 wherein said ligands are selected from the group consisting of transferrin, epidermal growth factor, insulin, asialoorosomucoid, mannose-6-phosphate, mannose, LewisX, sialyl LewisX, N-acetyllactosamine, galactose, glucose, and thrombomodulin; said fusogenic agents are selected from the group consisting of polymixin B and hemaglutinin H2; and said nucleus localization signal is T-antigen.

23. A composition for delivery of a selected nucleic acid into a host cell comprising a mixed-polymeric-micelle/nucleic-acid complex in an aqueous medium, wherein the mixed-polymeric-micelle/nucleic-acid complex comprises (a) a mixture of an amphiphilic polyester-polycation copolymer and an amphiphilic polyester-sugar copolymer, and (b) an effective amount of said selected nucleic acid.

24. The composition of claim 23 wherein said polyester polycation copolymer is a diblock copolymer comprising a hydrophobic polyester block bonded to a hydrophilic polycation block by an amide linkage.

25. The composition of claim 24 wherein said polyester block is a member selected from the group consisting of poly(L-lactic acid), poly(D-lactic acid), poly(D-,L-lactic acid), poly(glycolic acid), poly(L-lactic-co-glycolic acid), poly(D-lactic-co-glycolic acid), poly($\epsilon$-caprolactone), polybutyrolactone, and polypropiolactone.

26. The composition of claim 25 wherein said polyester block is poly(L-lactic acid).

27. The composition of claim 25 wherein said polyester block has a molecular weight of about 500 to 10,000.

28. The composition of claim 24 wherein said polycation block is a member selected from the group consisting of poly(L-serine ester), poly(D-serine ester), poly(L-lysine), poly(D-lysine), polyornithine, and polyarginine.

29. The composition of claim 28 wherein said polycation block is poly(L-serine ester).

30. The composition of claim 28 where polycation block has a molecular weight of about 500 to 10,000.

31. The composition of claim 23 wherein said polyester-sugar copolymer comprises a hydrophobic polyester segment and a hydrophilic sugar segment.

32. The composition of claim 31 wherein said polyester segment is a member selected from the group consisting of poly(L-lactic acid), poly(D-lactic acid), poly(D-,L-lactic acid), poly(glycolic acid), poly(L-lactic-co-glycolic acid), poly(D-lactic-co-glycolic acid), poly($\epsilon$-caprolactone), polybutyrolactone, and polypropiolactone.

33. The composition of claim 32 wherein said polyester segment is poly(L-lactic acid).

34. The composition of claim 32, wherein said polyester segment has a molecular weight of about 500 to 10,000.

35. The composition of claim 31 wherein said sugar segment comprises a polysaccharide.

36. The composition of claim 31 wherein said sugar segment comprises a glycosylated polymer.

37. The composition of claim 36 wherein said glycosylated polymer comprises at least one sugar moiety selected from the group consisting of galactose, glucose, fucose, fructose, lactose, sucrose, mannose, cellobiose, nytrose, triose, dextrose, trehalose, maltose, galactosamine, glucosamine, galacturonic acid, glucuronic acid, gluconic acid, and lactobionic acid.

38. The composition of claim 37 wherein said sugar moiety is lactobionic acid.

39. The composition of claim 36 wherein said glycosylated polymer comprises a polymer moiety selected from the group consisting of poly(L-serine ester), poly(D-serine ester), poly(L-lysine), poly(D-lysine), polyornithine, and polyarginine.

40. The composition of claim 39 wherein said polymer moiety is poly(L-serine ester).

41. The composition of claim 39 wherein said polymer moiety is poly(L-lysine).

42. The composition of claim 23 comprising about 5 to 95% by weight of said polyester-polycation copolymer.

43. The composition of claim 23 wherein said mixture further comprises a copolymer comprising (i) a hydrophobic portion, (ii) a hydrophilic portion bonded to the hydrophobic portion, and (iii) a functional moiety coupled to the hydrophilic portion, wherein said functional moiety is a member selected from the group consisting of a ligand, a fusogenic agent, a lysosomotrophic agent, a nucleus localizing signal, and mixtures thereof.

44. The composition of claim 43 wherein said ligand is a member selected from the group consisting of transferrin, epidermal growth factor, insulin, asialoorosomucoid, mannose-6-phosphate, mannose, LewisX, sialyl LewisX, N-acetyllactosamine, galactose, glucose, and thrombomodulin; said fusogenic agent is a member selected from the group consisting of polymixin B and hemaglutinin H2; and said nucleus localization signal is T-antigen.

45. A method for delivering a selected nucleic acid into a host cell comprising administering an effective amount of a mixed-polymeric-micelle/nucleic-acid complex in an aqueous medium, wherein the mixed-polymeric-micelle/nucleic-acid complex comprises (a) a mixture of an amphiphilic polyester-polycation copolymer and an amphiphilic polyester-sugar copolymer comprising a sugar moiety, and (b) an effective amount of said selected nucleic acid, such that said mixed-polymeric-micelle/nucleic-acid complex contacts the host cell and said sugar moiety triggers receptor mediated endocytosis of the mixed-polymeric-micelle/nucleic-acid complex, thus delivering said nucleic acid into the host cell.

46. The method of claim 45 wherein said sugar moiety is galactose and said host cell is a hepatocyte.

47. The method of claim 45 wherein said sugar moiety is mannose and said host cell is a macrophage.

48. The method of claim 45 wherein said sugar moiety is N-acetyllactosamine and said host cell is a T cell.

49. The method of claim 45 wherein said sugar moiety is glucose and said host cell is a colon carcinoma cell.

50. The method of claim 45 wherein said sugar moiety is galactose and said host cell is a melanoma cell.

* * * * *